US006498192B1

(12) United States Patent
Johnson et al.

(10) Patent No.: US 6,498,192 B1
(45) Date of Patent: Dec. 24, 2002

(54) PREVENTION OF APOPTOSIS IN NON-CANCEROUS CELLS

(75) Inventors: Leonard R. Johnson, Memphis, TN (US); Ramesh M. Ray, Cordova, TN (US); Mary Jane Viar, Memphis, TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/649,763

(22) Filed: Aug. 28, 2000

Related U.S. Application Data
(60) Provisional application No. 60/151,528, filed on Aug. 30, 1999.

(51) Int. Cl.$^7$ ............... A61K 31/195; A61K 31/235; A61K 31/155
(52) U.S. Cl. ............ 514/564; 514/561; 514/632; 514/544
(58) Field of Search .................. 514/544, 564, 514/632

(56) References Cited

U.S. PATENT DOCUMENTS

| | | | |
|---|---|---|---|
| 5,002,879 A | | 3/1991 | Bowlin et al. |
| 5,614,557 A | * | 3/1997 | Bey et al. ............ 514/34 |
| 6,258,845 B1 | * | 7/2001 | Gerner et al. ......... 514/544 |

OTHER PUBLICATIONS

Chen, et al., "p53 levels, functional domains, and DNA damage determine the extent of the apoptotic response of tumor cells", Genes & Development, 10:2438–2451 (1996).

Grassilli, et al., "Is polyamine decrease a common feature of apoptosis? Evidence from γ rays–and heat shock–induced cell death", Biochemical and Biophysical Research Communications, 216(2):708–714 (1995).

Packham and Cleveland, "Ornithine decarboxylase is a mediator of c–Myc–Induced apoptosis", Molecular and Cellular Biology, 14(9):5741–5747 (1994).

Poulin et al., "Induction of apoptosis by excessive polyamine accumulation in ornithine decarboxylase–overproducing cells", Biochem J., 311:723–727 (1995).

Tobias and Kahana, "Exposure to ornithine results in excessive accumulation of putrescine and apoptotic cell death in ornithine decarboxylase overproducing mouse myeloma cells", Cell Growth & Differentiation, 6:1279–1285 (1995).

Xie et al., "Loss of intracellular putrescine pool–size regulation induces apoptosis", Experimental Cell Research, 230:386–392 (1997).

Brooks, WH, "Polyamine involvement in the cell cycle, apoptosis, and autoimmunity", Medical Hypotheses, 44:331–338 (1995).

Lin et al., "Camptothecin induces differentiation, tissue transglutaminase and apoptosis in cultured keratocytes", Experimental Dermatology, 7:179–183 (1998).

McCormack et al., "Polyamines influence transglutaminase activity and cell migration in two cell lines", American Journal of Physiology, 267 (Cell Physiol. 36): C706–C714 (1994).

* cited by examiner

*Primary Examiner*—Frederick Krass
(74) *Attorney, Agent, or Firm*—Howard Eisenberg, Esq.

(57) ABSTRACT

Treatment of normal, non-cancerous, animal cells with an agent that depletes polyamines within the cells results in an inhibition of apoptosis when the cells are exposed to an inducer of apoptosis. This inhibition of apoptosis is not observed, or is observed to a lesser extent, in similarly treated cancerous cells. The method of the invention is useful in obtaining preferential killing of cancer cells, as opposed to normal cells, due to anti-cancer therapy.

6 Claims, 8 Drawing Sheets

CaCo-2: Camptothecin-iduced apoptosis

A

CaCo-2: TNF-induced apoptosis

B

PREVENTION OF APOPTOSIS IN NON-CANCEROUS CELLS

This application is a continuation of pending U.S. Provisional Patent Application No. 60/151,528, filed Aug. 30, 1999.

Pursuant to 35 U.S.C. §202, it is hereby acknowledged that the U.S. Government has certain rights in the invention described herein, which was supported in part by grant DK16505 from the National Institutes of Health.

FIELD OF THE INVENTION

The invention pertains to the field of regulating apoptosis in cells. In particular, the invention relates to the field of regulating apoptosis in cancerous and in non-cancerous cells.

BACKGROUND OF THE INVENTION

Apoptosis, also referred to as "programmed cell death" (PCD) is a natural phenomenon in which a series of events occurs that leads to the death of the cell. PCD is essential in the development of organisms and bodily tissues. PCD is also important in the removal from the body of potentially deleterious cells, such as cancer cells, virally infected cells, and autoimmune effector cells.

Cancer cells are often treated with agents that induce apoptosis, such as radiation or antineoplastic chemicals. Unfortunately, these apoptosis-inducing agents also exert their effects to some degree on non-neoplastic cells. This may result in the death of normal tissue adjacent to a cancer that is treated by radiation, or in serious local or systemic side effects when treating cancers with antineoplastic drugs.

An ideal anti-cancer therapeutic agent is one which kills cancer cells but which spares normal, non-cancerous cells. Such a therapy would permit the aggressive treatment of cancers without the risk of serious side effects. Consequently, a significant need exists for a method that protects normal, non-cancerous cells from undergoing apoptosis when exposed to apoptosis-inducing agents but which does not protect cancer cells, or at least which protects cancer cells to a lesser degree.

SUMMARY OF THE INVENTION

The inventors have discovered that the depletion of polyamines within a cell inhibits apoptosis in non-cancerous cells, but has a much decreased effect, if any, on apoptosis in cancerous cells. This discovery has important implications for anti-cancer therapy, such as chemotherapy, immunotherapy, and radiation therapy, in which agents that induce apoptosis are delivered to cells within the body. Typically, non-cancerous cells, as well as the target cancerous cells, are exposed to the apoptosis-inducing agents. By inhibiting apoptosis within non-cancerous cells while not inhibiting, or inhibiting to a lesser degree, apoptosis in cancerous cells, normal tissue may be spared during such treatment to kill cancer cells.

The invention is applicable for in vitro and in vivo experimental and therapeutic purposes. Cells, both normal and cancerous, may be from any animal, such as humans and domestic animals like dogs and cats. Likewise, patients that may benefit from the method of the invention may be human or veterinary patients, such as dogs and cats.

In one embodiment, the invention is a method for inhibiting apoptosis in normal, that is non-cancerous, cells which method includes the steps of depleting the level of polyamines within the cell and inhibiting apoptosis in the cell. In a preferred embodiment, the depletion of the level of polyamines within the cell is by inhibiting the intracellular enzyme ornithine decarboxylase (ODC). In a particularly preferred embodiment, ODC is inhibited by administering DL-œ-difluoromethylornithine (DFMO) to the cell. Preferably, the level of each of the polyamines; putrescine (PUT), spermidine (SPD), and spermine (SPM), are depleted, although in some situations in accordance with the method of the invention, PUT and SPD levels may be depleted and SPM levels may not be depleted.

In this specification, the term "polyamine" refers to spermidine, spermine, and their diamine precursor, putrescine. For purposes of this specification the terms "depleted", "depletion", or "depleting", when referring to intracellular levels of any or all of the polyamines, PUT, SPD, and SPM, means that the level of the measurable polyamine within the non-cancerous cell is reduced sufficiently to inhibit apoptosis. Generally, intracellular PUT levels are reduced before SPD levels, which are reduced before SPM levels. In cell culture, PUT levels tend to become depleted within an hour, SPD within 2 days, and SPM after about 4 days following the initiation of treatment with an ODC inhibitor. The effect of depletion of polyamines in accordance with the invention to inhibit apoptosis in normal cells is usually observable within the first two days, even before the levels of SPM begin to drop. Similar patterns are observed with in vivo ODC inhibition therapy in live animals.

In accordance with the method of the invention, measurable PUT in the cell is generally reduced by 50% or more, preferably by 80% or more, and most preferably by 100% from the pre-treatment level. SPD levels are typically reduced by 30% or more, preferably by 50% or more, and most preferably by 80% or more from the pre-treatment level. SPM levels may not be reduced by the time that an inhibition of apoptosis in accordance with the method of the invention is observed. Generally, beginning several days, such as 2 to 4 days, following the initiation of therapy, SPM levels are reduced by 10% or more, preferably by 30% or more, and most preferably by 50% or more from the pretreatment level. However, the actual level of reduction of each or all of the polyamines is immaterial, so long as the level of polyamines is reduced sufficiently to inhibit apoptosis in normal cells, that is to achieve depletion of the polyamines.

In another embodiment, the invention is a method for selectively inhibiting apoptosis in normal, non-cancerous cells, while not inhibiting apoptosis, or inhibiting apoptosis to a lesser degree, in cancerous cells. The method of the invention according to this embodiment includes administering to a patient suffering from a cancer an effective amount of an agent that causes the depletion of the level of polyamines within the normal, non-cancerous cells, and inhibiting apoptosis in the normal cells, and which agent inhibits apoptosis to a lesser extent or not at all in the cancerous cells. In a preferred embodiment, the depletion of the level of polyamines is by inhibiting ODC. In a particularly preferred embodiment, ODC is inhibited by administering DFMO to the patient. Preferably, the level of each of the polyamines; putrescine (PUT), spermidine (SPD), and spermine (SPM), are depleted, although as stated above, levels of intracellular PUT are depleted before the levels of SPD, which are in turn depleted before the levels of SPM, and apoptosis in normal tissues may be inhibited before depletion of all the polyamines.

In accordance with the invention, the depletion of the polyamines typically occurs in cancerous cells, similarly to the depletion seen in normal cells. However, unlike what occurs with normal cells, the depletion of polyamines in cancerous cells does not result in an inhibition of apoptosis.

In another embodiment, the method of the invention is a method for treatment of a patient with cancer, which method includes administering to the patient an effective amount of an agent that causes the depletion of polyamines within cells, such as an inhibitor of ODC, depleting the polyamines in the patient's cells, and exposing cancer cells and normal cells within the body of the patient to an apoptosis-causing agent, thereby killing the cancer cells and not killing the normal cells, or killing the normal cells at a reduced rate compared to the cancer cells. The patient may be any animal, such as a human or a veterinary patient, including dogs, cats, and ferrets, and livestock such as cattle, horses, goats, sheep, and pigs. The apoptosis-causing agent may be anything that induces apoptosis, such as a chemical agent, like an antineoplastic drug, an immunotherapeutic agent, or an electromagnetic or acoustic ray, such as an x-ray or gamma ray. Preferably, the ODC inhibitor is DFMO.

BRIEF DESCRIPTION OF THE FIGURES

FIG. 1A is a graph comparing the number of floating cells in control vs. camptothecin exposed cells. FIG. 1B is a graph comparing the activity of caspase 3 in attached and floating cells, which cells are either control cells or were exposed to camptothecin. FIG. 1C is a DNA fragmentation analysis from attached and floating cells, which cells were either control or camptothecin-exposed cells.

FIG. 2A is a graph comparing the percentage of floating cells exposed or not exposed to camptothecin in control cells and in cells protected by treatment with DFMO. FIG. 2B is a graph comparing the activity of caspase 3 in control cells and in DFMO protected cells.

FIG. 3A is a graph comparing the number of floating cells over time in control and in DFMO treated cells. FIG. 3B is a graph comparing the activity of caspase 3 in these two cell groups.

FIG. 5A shows that putrescine accumulates in cells following exposure to DEGBG, and FIGS. 5B and 5C show that the spermidine and spermine levels, respectively, are not significantly increased by exposure to DEGBG.

FIG. 8A compares the number of floating cells in control vs. camptothecin treated cells when treated or not treated with DFMO.

FIG. 8B compares the number of floating cells in control vs. TNF exposed cells when treated or not treated with DFMO.

DETAILED DESCRIPTION OF THE INVENTION

Figure 1:
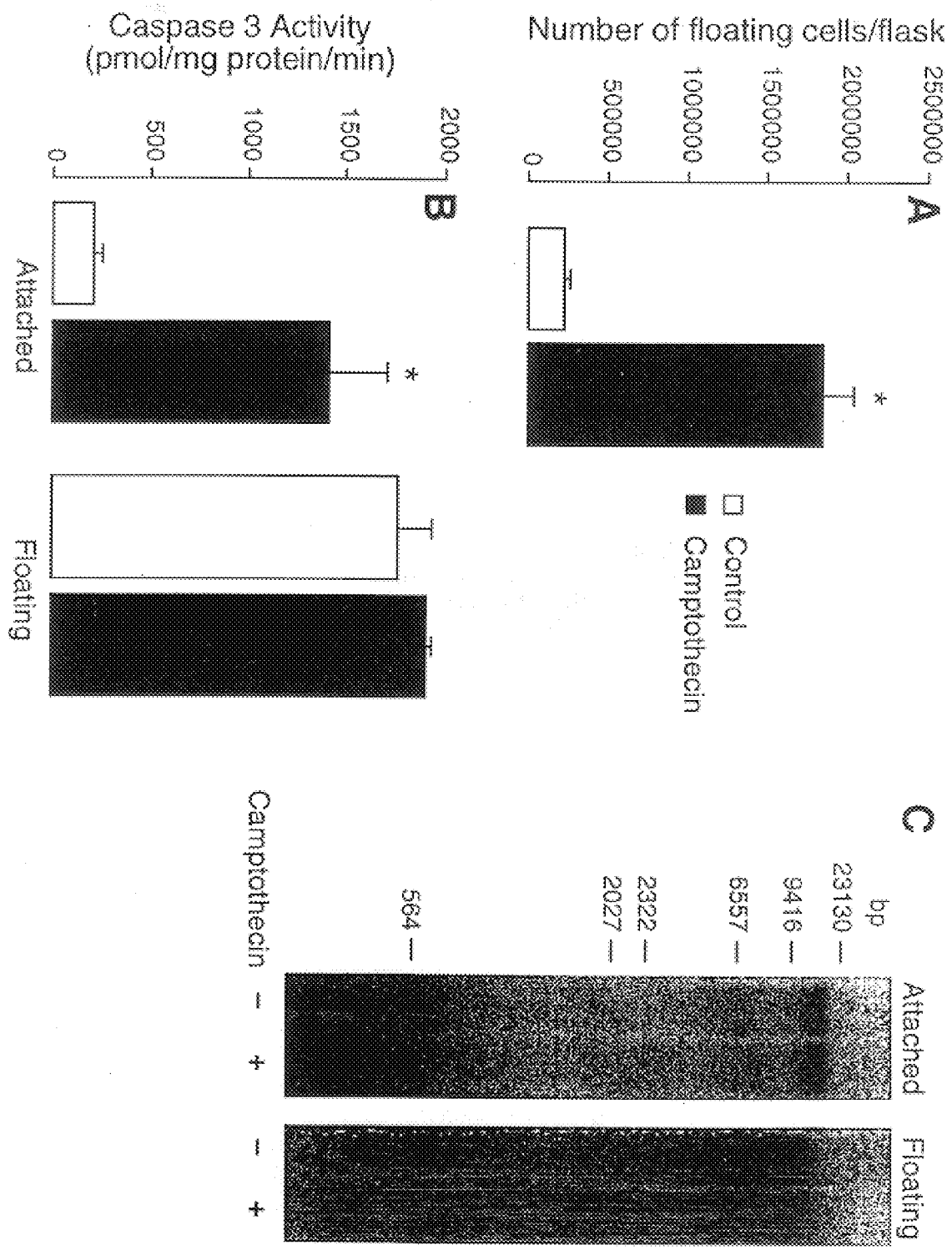
FIGS. 1A, 1B, and 1C show a comparison of indices of apoptosis in cells exposed to the apoptosis-inducing agent camptothecin and in control cells.

In a preferred embodiment, the invention is a method for preferentially inhibiting apoptosis in non-neoplastic cells compared to neoplastic cells that are exposed to a similar apoptosis-inducing event. The method of the invention inhibits apoptosis in non-cancerous cells while not inhibiting, or inhibiting to a lesser extent, apoptosis in cancer cells. The cells, normal and/or cancer cells, may be within the body of an animal, such as a human or veterinary patient, or may be outside of the body of an animal, such as in a cell culture or a surgically removed biopsy sample.

In accordance with the preferred method of the invention, an inhibitor of ODC is administered to the cells, the level of polyamines, especially that of putrescine, in the cells is depleted, and apoptosis is inhibited in normal cells and is not inhibited, or is inhibited to a lesser extent, in cancer cells.

The inhibitor of ODC may be any organic or inorganic molecule that prevents ODC from catalyzing the formation of putrescine. Preferably, the inhibitor of ODC is DFMO. However, any inhibitor of ODC may be employed in accordance with the preferred embodiment of the invention, so long as the inhibitor does not itself cause death of normal cells.

Preferably, each of the three polyamines, putrescine, spermidine, and spermine, are depleted from the cell. However, in certain instances and in accordance with the invention, only PUT and SPD levels may be reduced, with retention of the pre-treatment level of SPM. Depletion of polyamines, as used in this specification, refers to depletion of measurable polyamines within the cell.

In the examples that follow, apoptosis in normal cells, with and without inhibition of ODC, is illustrated in a limited number of cell types, including normal rat epithelial cells. It is understood, however, that the invention is applicable to cells other than rat cells, such as human, dog, or cat cells. For example, the method of the invention may be applied to neoplastic and non-neoplastic cells of ectodermal, mesodermal, or endodermal origin from any animal species.

In accordance with the method of the invention, the ODC-inhibiting agent may be administered to a patient in need of therapy by any suitable route for the particular agent. For example, a chemical ODC inhibitor may be administered orally, by intramuscular, subcutaneous, or intravascular injection, or by administration directly into a tissue, such as by direct injection into a tumor and/or surrounding non-neoplastic tissues. Other suitable means of administering a chemical ODC inhibitor to a patient include ophthalmic application, suppositories, intradermal administration, and transmucosal administration, such as by intranasal droplets, lozenges or a gargle.

In accordance with the invention, the ODC inhibitor, such as DFMO, is administered to a cell or a patient in an amount effective to inhibit the catalytic action of ODC in the first rate-limiting step in intracellular polyamine biosynthesis and in an amount below that which will result in death of the cell or of the patient. As an example, a suitable range of DFMO for administration to a mammal, such as a human, is preferably between 10 mg/kg to 200 mg/kg per day. However, if desired, amounts higher or lower than this range may be administered, so long as the amount of DFMO administered is high enough to inhibit ODC and not so high as to seriously injure or kill the cell or patient. In human patients, the DFMO may be administered orally in a tablet or capsule form containing 100 to 500 mg of DFMO, which is administered 1 to 10 times daily to achieve the desired effect.

The examples that follow are illustrative of the invention and are not to be construed as limiting the invention.

EXAMPLE 1
Non-cancerous Cells

IEC-6 cells, having the ATCC designation CRL-1592, were obtained from the American Type Culture Collection at passage 13. The IEC-6 cells are normal, non-cancerous intestinal epithelial cells derived from fetal rat crypt cells. These cells are non-tumorigenic and retain the undifferentiated character of epithelial stem cells.

The IEC-6 cell stock was maintained in T-150 flasks in a humidified, 37° C. incubator in an atmosphere of 90:10 air:CO2. The medium used was Dulbecco's modified Eagle medium (DMEM) (Gibco BRL, Grand Island, N.Y.) with 5% heat inactivated fetal bovine serum (FBS) (Sigma, St. Louis, Mo.) and 10 $\mu$g insulin and 50 $\mu$g gentamicin sulfate per ml. The stock was passaged weekly at 1:10, fed 3 times per week, and passages 15–20 were used.

The cells were plated on day 0 at a density of $6.25 \times 10^4$ cells/m² in T-150 flasks in DMEM/dFBS (dialyzed fetal bovine serum with 10,000 molecular weight cut-off) (Sigma, St. Louis, Mo.) with or without the treatment compound or compounds described in the Examples that follow. The cells were fed on day 2. On day 3, medium was removed and replaced with serum-free medium.

EXAMPLE 2
Evaluation of Apoptosis in Normal Cells

On day 4, camptothecin (Sigma, St. Louis, Mo.) in a DMSO vehicle was added to a concentration of 20 $\mu$M into the serum-free medium containing the cells of Example 1 for 3 to 18 hours, with the vehicle (DMSO) added to controls. Detachment-induced cell death (DICD) is a well recognized form of apoptosis in anchorage-dependent cell types, such as intestinal epithelial cells. Floating cells were poured into a 25 ml tube and the monolayer was washed once with HBSS without calcium and magnesium. This wash was then combined into the tube with the floating cells. Attached cells were taken up with 0.05% trypsin plus 0.53 MM EDTA, followed by one wash of the flask with DMEM/5% FBS. Cell counts were determined separately for floating and attached cells by counting on a Model $Z_F$ Coulter counter. Floating cells were expressed as a percentage of the total cell count obtained by combining the number of floating and attached cells. As shown in FIG. 1A, there was an 8-fold increase in the number of floating cells in the camptothecin treated group as compared to the DMSO control group within 6 hours of treatment.

In a separate flask, following camptothecin or DMSO addition, the cells were harvested after 16 hours in order to obtain a sufficient number of floating cells for analysis. Floating cells were then poured off to be counted and were combined with one wash with cold DPBS (Sigma, St. Louis, Mo.). The attached cells were then harvested for determination of caspase activity. 10 ml of DPBS was added to the flask and the monolayer was scraped and collected into a 25 ml tube. The flask was washed once with 10 ml of DPBS and combined into the 25 ml tube. The cells were pelleted by centrifugation at 800×g for 5 minutes. The supernatant was discarded and the pellet was resuspended in 1 ml of cold DPBS and transferred into a microfuge tube. The cells were pelleted by centrifugation at 10,000×g at 4° C. for 10 minutes. The supernatant was discarded and the cells were lysed in 100 ml of ice cold cell lysis buffer (50 mM HEPES, pH 7.4, 0.1% CHAPS, 1 mM DTT, 0.1 mM EDTA, 0.1% NP40) (Sigma, St. Louis, Mo.). The assay for caspase activity was carried out in a 96-well plate. Into each well was placed 20 $\mu$l of cell lysate, 70 $\mu$l of assay buffer (50 mM HEPES, pH 7.4, 0.1% CHAPS, 100 mM NaCl, 10 mM DTT, 1 mM EDTA ) and 10 $\mu$l of caspase 3 colorimetric substrate (2 mM DEVD-pNA prepared in assay buffer, a caspase specific peptide that is conjugated to the chromogen p-nitroanilide) (Biomol Research Laboratories, Plymouth Meeting, Pa.). The 96-well plate was incubated at 37° C. for 2 hours, during which time the caspase in the sample was allowed to cleave the chromophore pNA from the substrate molecule. Absorbance readings at 405 nm were made after the 2 hour incubation, with the caspase activity being directly proportional to the color reaction. Protein was determined for each sample using the BCA method (Pierce, Rockford, Ill.) and a standard curve for p-nitroanilide was carried out. Results for caspase activity were expressed as pmol of pNA released/mg protein/minute.

Cells were collected for determining the presence or absence of DNA fragmentation. After treatment with camptothecin (or vehicle), floating cells were poured off and combined with one DPBS wash of the monolayer. Cells were pelleted, by centrifugation at 800×g for 5 minutes. The supernatant was discarded and the pellet was resuspended in 100 $\mu$l of resuspension buffer. The attached cells were collected for DNA fragmentation by scraping in DPBS and combining with one wash of the flask with DPBS. Cells were pelleted at 800×g for 5 minutes, the supernatant was discarded and the pellet was resuspended in 100 $\mu$l of resuspension buffer. The nucleosomal fragmentation assay was carried out by isolating DNA from the cells using the TACS apoptotic DNA laddering kit (Trevigen, Gaithersburg, Md.) and analyzing the labeled DNA by agarose gel electrophoresis following the manufacturer's instructions.

As shown in FIGS. 1B and 1C, attached cells showed a 7-fold increase in caspase 3 activity, but did not show remarkable DNA fragmentation. FIGS. 1B and 1C show that detached cells from both control and camptothecin treated groups showed characteristic nucleosomal DNA fragments and increased caspase 3 activity.

The results establish that camptothecin is an effective inducer of apoptosis in the IEC-6 cells and that caspase 3 activity is well correlated with DNA fragmentation associated with apoptosis. Because caspase 3 levels indicate the occurrence of apoptosis, caspase 3 activity was used as an indicator of the initiator phase of apoptosis in the Examples that follow.

EXAMPLE 3
Polyamine Depletion

IEC-6 cells were grown for 4 days in the presence or absence of DFMO (Marion Merrel Dow, Cincinnati, Ohio) the highly specific inhibitor of ODC. DFMO treatment depletes putrescine within 3 hours. Depletion of spermidine requires 24 hours and significant depletion (about 50%) of spermine requires 3 days.

Figure 2:
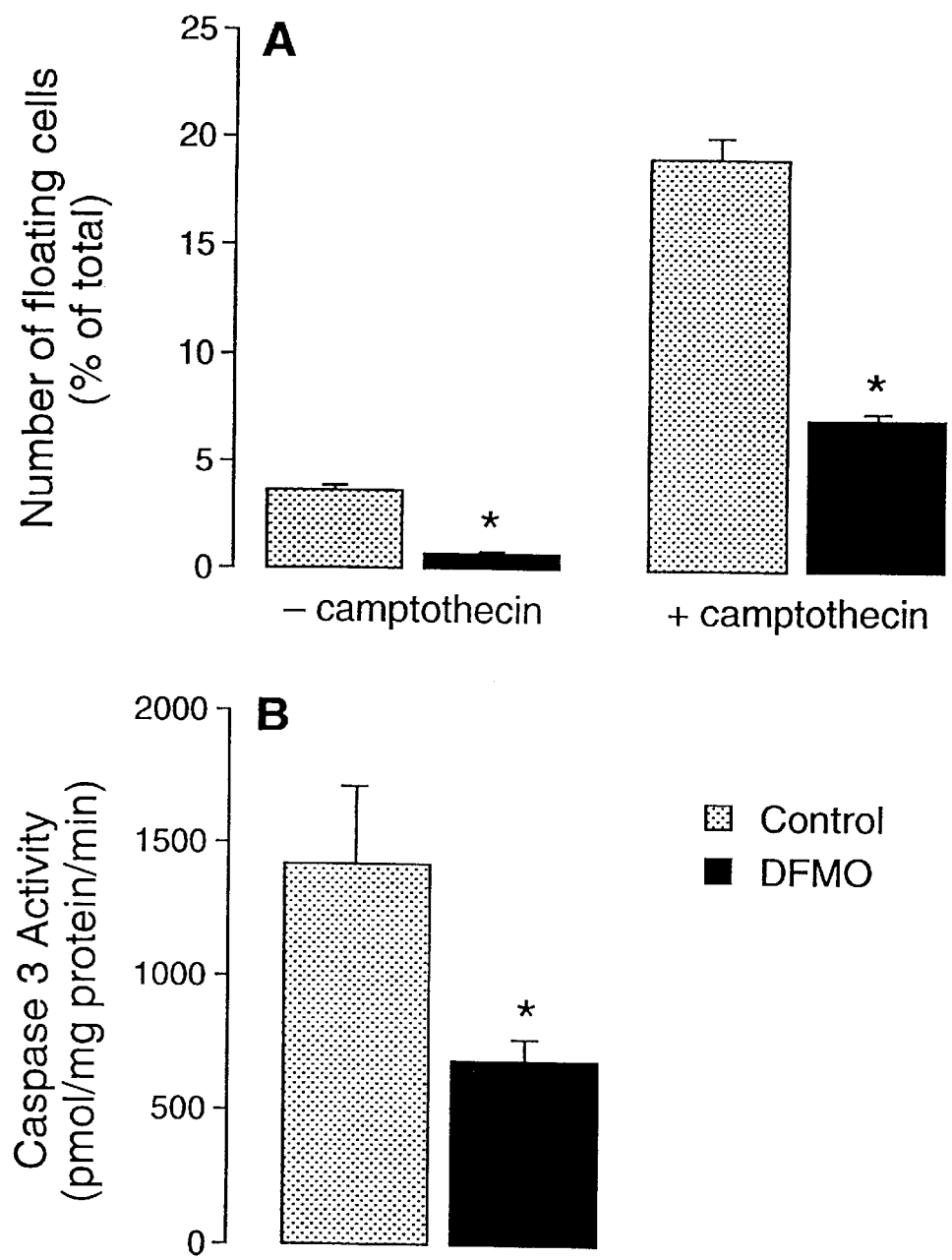
FIGS. 2A and 2B show a comparison of indices of apoptosis in floating and in attached cells demonstrating that polyamine depletion inhibits camptothecin-induced apoptosis in non-cancerous cells.

Camptothecin-induced apoptosis was determined 6 hours after camptothecin treatment. As shown in FIG. 2, cells treated with DFMO (polyamine depleted) were protected against both DMSO (vehicle) and camptothecin-induced apoptosis. About a 3-fold decrease in the number of floating cells was observed in polyamine depleted cells as compared to control cells treated with camptothecin, as shown in FIG. 2A. DFMO treatment also resulted in approximately 50% lower caspase 3 activity compared to control, as shown in FIG. 2B.

EXAMPLE 4

Time Course of Induction of Apoptosis

Figure 3:
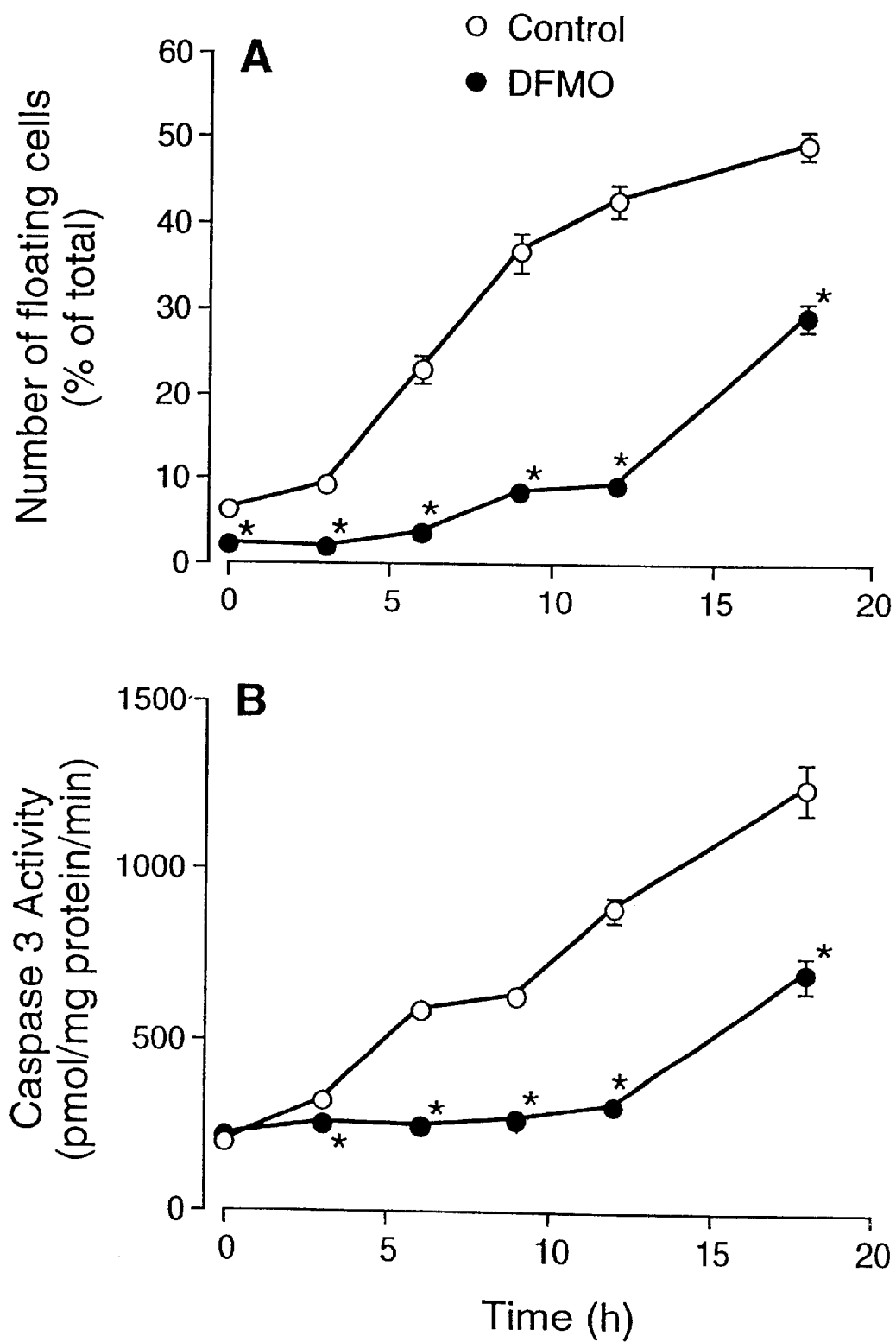
FIGS. 3A and 3B show a comparison of indices of apoptosis over time in control cells and in DFMO protected cells.

As shown in FIG. 3A, camptothecin induced apoptosis (as judged by the number of floating cells) began within 3 hours and increased progressively up to 18 hours (from 6.2% at 0 time to 49.3% at 18 hours) in control cells. The onset of apoptosis was delayed in DFMO treated cells for up to 12 hours (from 2.2% at 0 time to 9.3% at 12 hours) and reached maximum of 29.1% at 18 hours. As described in Example 2, attached cells were collected for the determination of caspase 3 activity. Caspase 3 activity increased progressively with time in control cells. In contrast, DFMO treated cells did not show remarkable increases in caspase 3 activity for up to 12 hours. In these cells, significant increase in caspase 3 activity was observed only after 18 hours of exposure to camptothecin, as shown in FIG. 3B. These results indicate that polyamine depletion delays the onset of apoptosis in IEC-6 cells, and suggest that the intracellular polyamine levels may be a critical factor in the regulation of spontaneous apoptosis.

EXAMPLE 5

Addition of Exogenous Polyamines

Figure 4:
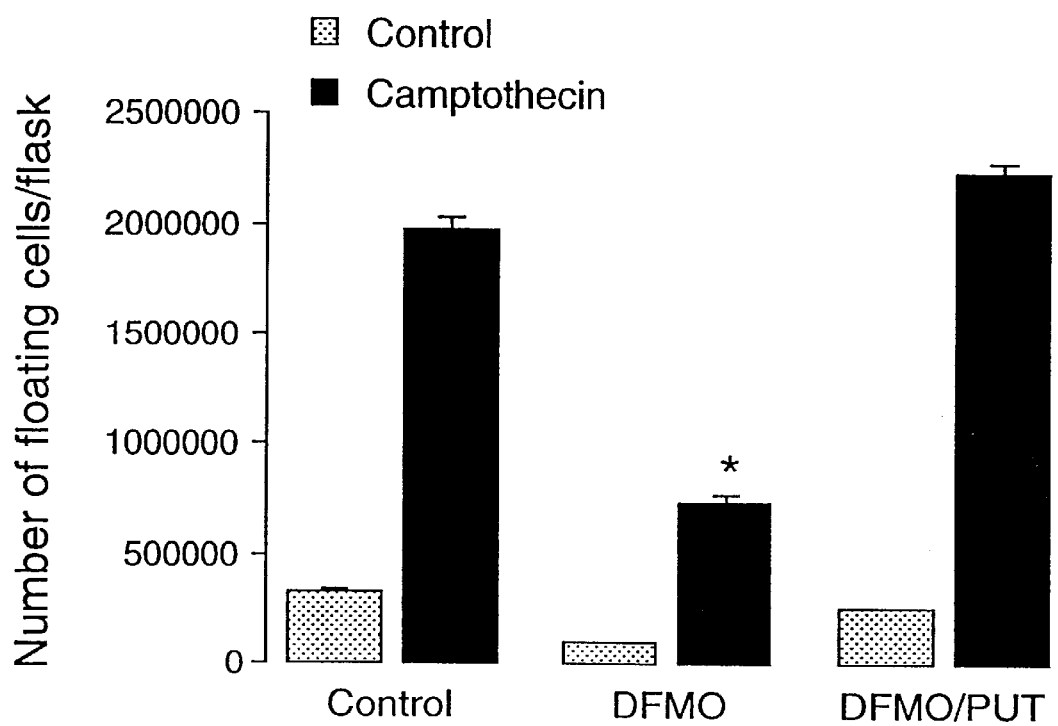
FIG. 4 is a graph comparing the number of floating cells in control and camptothecin exposed cells and in these cells following treatment with DFMO or with DFMO and putrescine.

As shown in FIG. 4, DFMO again decreased the number of floating cells as compared to control. Addition of exogenous 10 $\mu$M putrescine along with DFMO restored the number of floating cells to control levels. DNA fragmentation was evident in floating cells irrespective of the treatment, but attached cells did not clearly reveal nucleosomal fragments.

EXAMPLE 6

Levels of Polyamines

IEC-6 cells were grown, as described in the above Examples, but in the presence of either DFMO (control) or diethylglyoxal bis-(guanylhydrazone) (DEGBG). DFMO inhibits the enzyme ornithine decarboxylase (ODC), which catalyzes a step in the production of putrescine. DEGBG blocks the conversion of putrescine to the polyamines spermidine and spermine by inhibiting the enzyme S-adenosyl methionine decarboxylase (SAMDC).

Intracellular polyamines were analyzed by high performance liquid chromatography. Cells were plated in 60 mm dishes at 6.25×10$^4$ cells/cm$^2$ and grown in DMEM/dFBS with or without DFMO or DEGBG. After washing the monolayer three times with ice-cold DPBS, 0.5 M perchloric acid was added and the samples were then frozen at −80° C. until ready for extraction, dansylation, and HPLC. The standard curve encompassed the range of 0.31–10 $\mu$M. Values that fell >25% below the curve were considered not detectable. The level of polyamine was determined by the Bradford method, as described in Anal. Biochem., 72:248–254 (1976).

Figure 5:
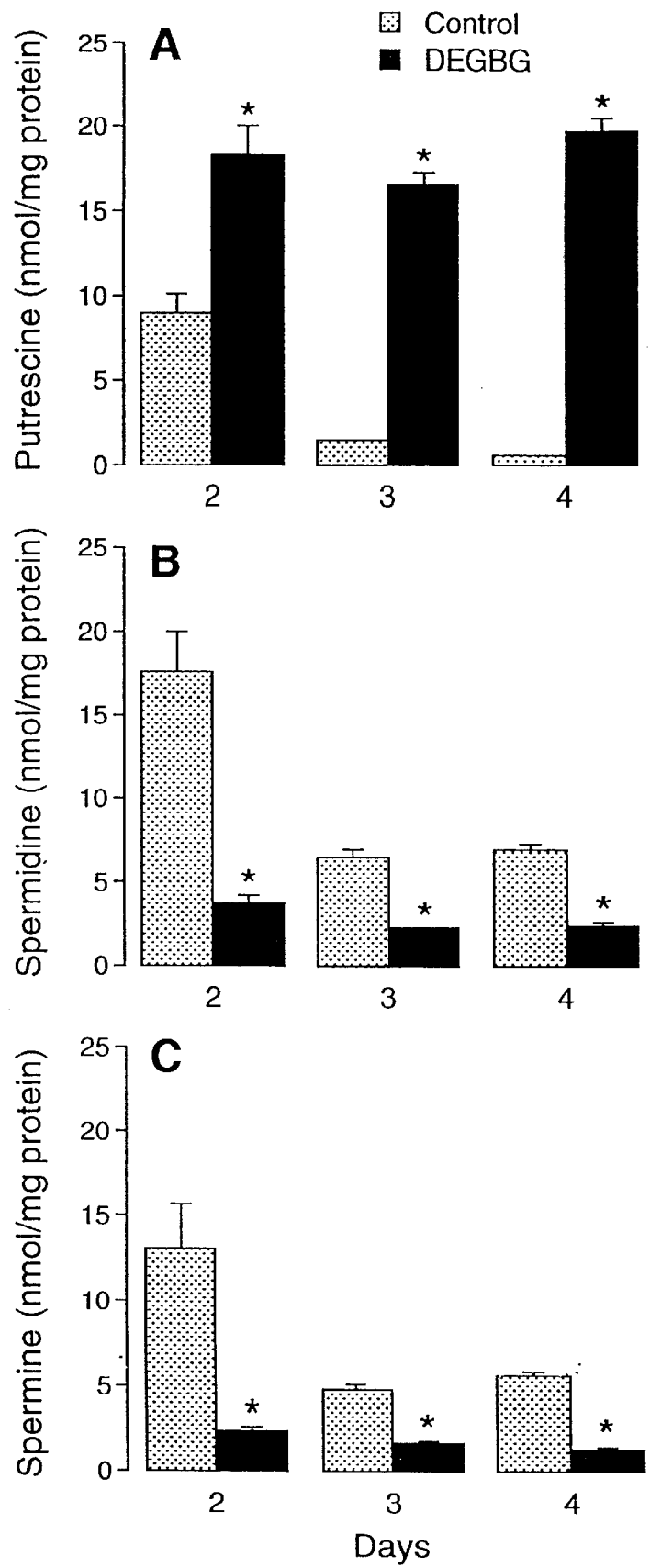
FIG. 5 is a series of graphs showing the effects of DEGBG on the levels of polyamines.

As shown in FIGS. 5A, 5B, and 5C, DEGBG significantly increased the level of putrescine in the cells while decreasing the levels of spermidine and spermine. In contrast, control cells grown in the presence of DFMO had decreases in each of the three polyamines.

These results establish that inhibition of ODC results in depletion of all three polyamines. In contrast, inhibition of SAMDC leads to an accumulation of putrescine and concomitant depletion of spermidine and spermine.

EXAMPLE 7

Apoptosis in ODC and in SAMDC Inhibited Cells

Figure 6:
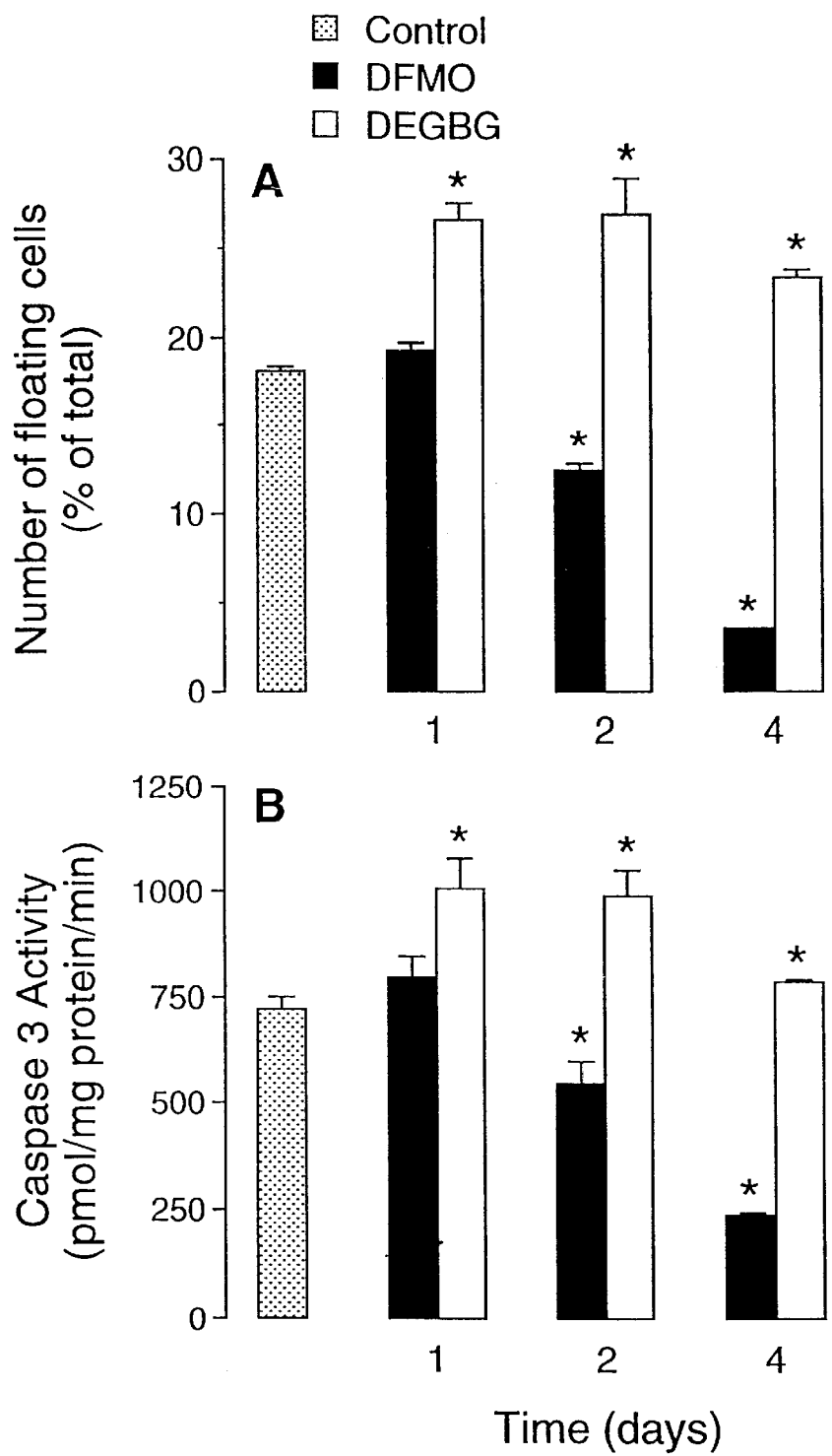
FIG. 6A shows a comparison in number of floating cells.
FIG. 6B shows a comparison level of caspace 3 activity following treatment with DFMO or DEGBG.

IEC-6 cells were grown in the presence of DMSO (control), DFMO, or DEGBG. As shown in FIG. 6A, DFMO treatment led to a progressive decrease in the percentage of floating cells over days 1, 2, and 4 (19.2, 12.4, and 2.2%). When compared to control (18.8%), DFMO treatment for only 1 day, which results in putrescine depletion, but not spermidine or spermine depletion, did not effect the percentage of floating cells. In contrast, DEGBG treatment showed a significant increase in the percentage of floating cells on days 1, 2, and 4 (26.6, 26.9, and 23.3%) as compared to DFMO treated cells, as well as to control cells. Caspase 3 activity, as shown in FIG. 6B, followed the same pattern as that for the number of floating cells.

These results show that the accumulation of putrescine is associated with the induction of apoptosis, while depletion of spermidine and spermine leads to the inhibition of apoptosis in IEC-6 cells.

EXAMPLE 8

Caspase 3 Levels

Total cell protein (50 $\mu$g) from cell extracts prepared for caspase 3 assay was separated on 15% SDS-PAGE and transferred to nitrocellulose membranes for western blotting. Equal loading of protein was confirmed by staining the nitrocellulose membrane with Ponceau S (Sigma, St. Louis, Mo.). The membrane was then probed with an antibody directed against caspase 3 (CPP32) (Santa Cruz Biotechnology, Santa Cruz, Calif.). The immunocomplexes were visualized by the enhanced chemiluminescence detection system.

Figure 7:
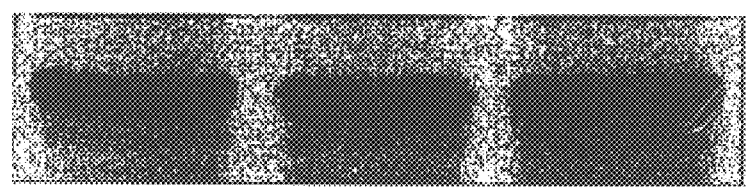
FIG. 7 shows a Western blot analysis of caspase 3 levels in control cells, in cells depleted of polyamines by treatment with DFMO, and in cells treated with both DFMO and putrescine.

As shown in FIG. 7, the level of caspase 3 was not significantly different in polyamine depleted cells (DFMO) compared with controls or cells treated with DFMO and putrescine. Putrescine was added to cell extracts from DFMO treated cells which were low in caspase 3 activity. Increasing putrescine concentration up to 5 $\mu$M did not reveal any effect on caspase activity.

These data show that the level of intracellular polyamines, rather than caspase activity, is the determinant of the inhibition of apoptosis.

EXAMPLE 9

Non-cancerous Human Cells

Studies described in Examples 1 to 8 are repeated, except that normal human intestinal cells are substituted for the IEC-6 rat intestinal cells. Similar inhibition of apoptosis is seen following treatment with DFMO.

EXAMPLE 10

Inhibition of ODC in Cancerous Cells

Studies described in Examples 1 to 8 are repeated, except that cancerous human intestinal CaCo-2 cells (ATCC no. HTB37) are substituted for the IEC-6 rat intestinal cell lines. No inhibition of apoptosis is observed following the treatment with DFMO.

EXAMPLE 11

Cancerous Cells

Figure 8:
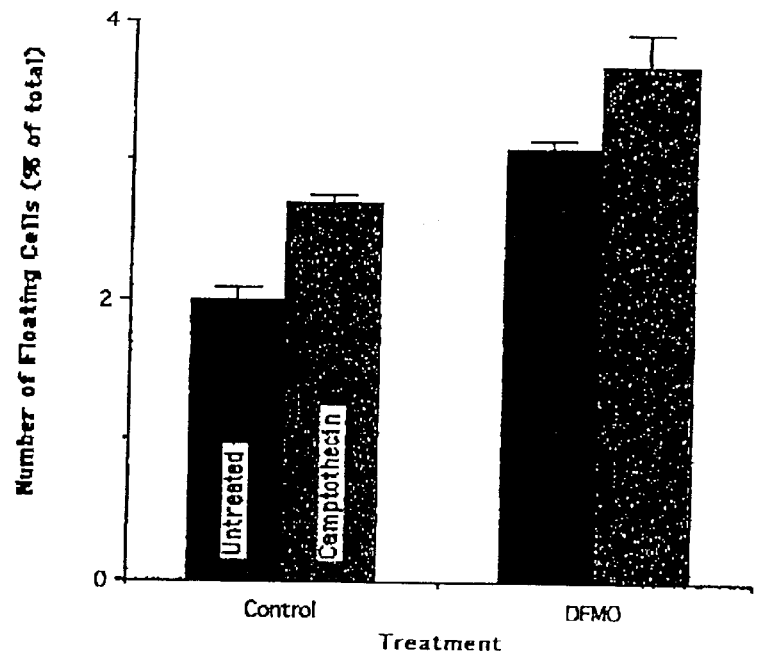
FIG. 8 is a series of bar graphs demonstrating the ineffectiveness of DFMO to inhibit apoptosis in cancer cells.
Figure 8:
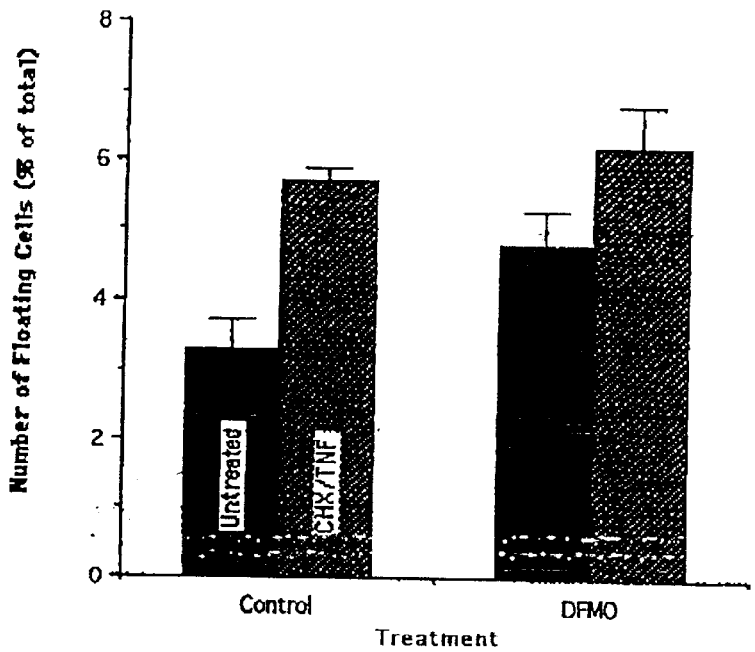

Cancerous human intestinal CaCo-2 cells were grown in similar culture media as described in Example 1, except that one group of the cells was grown in a medium not containing DFMO and another group was grown in a medium containing DFMO. After four days of growth, camptothecin at a dose of 20 μM was added to the culture medium of each of the groups. After 6 hours, the number of floating cells in the media of the two groups of cells was determined. The study was repeated using a different inducer of apoptosis, a combination of 20 ng/ml of tumor necrosis factor-α (TNF-α) and 25 μg/ml of cycloheximide. The results are shown in Table I and in FIG. 8, and clearly demonstrate that DFMO did not protect the cancerous cells from apoptosis induced by either of the agents.

TABLE I

Camptothecin

| | |
|---|---|
| Control (no DFMO): | Untreated (no camptothecin) = 2.0 =/− .09 |
| | Treated (camptothecin) = 2.7 +/− .06 |
| Treated (with DFMO): | Untreated (no camptothecin) = 3.1 +/− .06 |
| | Treated (camptothecin) = 3.7 +/− .24 |
| TNF-α and cycloheximide | |
| Control (no DFMO): | Untreated (no TNF-α + cycloheximide) = 3.3 +/− .4 |
| | Treated (TNF-α + cycloheximide) = 5.7 +/− .2 |
| Treated (with DFMO): | Untreated (no TNF-α + cycloheximide) = 4.8 +/− .5 |
| | Treated (TNF-α + cycloheximide) = 6.2 +/− .6 |

EXAMPLE 12

DFMO at a dosage of 100 mg/kg/day is administered orally for four days to an adult dog suffering from a mast cell tumor on one of its rear legs. The tumor is treated in multiple sessions by exposure to $Co^{60}$ gamma radiation as indicated for this type of tumor. The field of exposure to the radiation exceeds the boundaries of the tumor. Following therapy, the tumor is killed and a visually noticeable decrease in death of the surrounding normal tissues is observed compared with that typically observed with this type of therapy.

The scientific articles listed in the following list of References are incorporated herein by reference. Bowlin, et al., U.S. Pat. No. 5,002,879, is incorporated herein by reference. The articles, McCormack et al., Am. J. Physiol., vol. 267 (Cell Physiol. 36):C706–C714 (1994), and Ray et al., Am. J. Physiol., vol. 276 (Cell Physiol 45):C684–C691 (1999), are incorporated herein by reference. U.S. Provisional Patent Application No. 60/151,528 is incorporated herein by reference.

Although the above description contains many specificities, they should not be interpreted as limitations on the scope of the invention, but rather as illustrations. One skilled in the art will understand that many variations of the invention are possible and that these variations are to be included within the scope of the following claims.

REFERENCES

1. Aoshiba, K., S. I. Rennard, and J. R. Spurzern. Cell-matrix and cell-cell interactions modulate apoptosis of bronchial epithelial calls. Am. J. Physiol. 272 (Lung Cell. Mol. Physiol. 16): L28–L37, 1997.
2. Bates, R. C., A. Buret, D. F. van Helden, M. A. Horton, and G. F. Burns. Apoptosis induced by inhibition of intercellular contact J. Cell Biol. 125: 403–415, 1994.
3. Beaulieu, J. F. Differential expression of the VLA family of integrins along the crypt-villus axis in the human small intestine. J. Cell Sci. 102: 427–436, 1992.
4. Boudreau, N., C. J. Sympson, Z. Werb, and M. J. Bissell. Supression of ICE and apoptosis in mammary epithelial cells by extracellular matrix. Science 267: 891–893, 1995.
5. Bradford, M. A. A rapid and sensitive method for the quantitation of microgram quantities of protein utilizing the principle of dye binding. Anal. Biochem, 72: 224–254, 1976.
6. Brooks, W. H. Polyamine involvement in the cell cycle, apoptosis, and autoimmunity. Med. Hypothesis, 44: 331–338, 1995.
7. Chen, X., L. J. Ko, L. Jayraman, and C. Prives. p53 levels, functional domains, and DNA damage determine the effect of the apoptotic response of tumor cells. Genes Dev. 10, 2438–2451, 1996.
8. Davis, R. H., D. R. Morris, and P. Coffino. Sequestered end products and enzyme regulation: the case of ornithine decarboxylase. Microbiol. Rev. 56: 280–290, 1992.
9. Erhardt, P., K. J. Tomaselli, and G. M. Cooper. Identification of the MDM2 oncoprotein as a substrate for CPP32-like apoptotic proteases. J. Biol. Chem. 272: 15049–15052, 1997.
10. Farschon, D. M., C. Couture, T. Mustelin, and D. D. New-meyer. Temporal phases in apoptosis defined-by the actions of Src homology 2 domains, ceramide, Bcl-2, interleukin-1 converting enzyme family proteases, and a dense membrane fraction. J. Cell Biol. 137: 1117–1125, 1997.
11. Frisch, S. M., and H. Francis. Disruption of epithelial cell-matrix interactions induces apoptosis. J. Cell Biol. 124: 619–626, 1994.
12. Gavrieli, Y., Y. Sherman, and S. A. Ben-Sasson. Identification of programmed cell death in situ via specific labeling of nuclear DNA fragmentation. J. Cell Biol. 119: 493–501, 1992.
13. Gervais, F. G., N. A. Thornberry, S. C. Ruffolo, D. W. Nicholson, and S. Roy. Caspases cleave focal adhesion kinase during apoptosis to generate a FRNK-like popypeptide. J. Biol. Chem. 273: 17102–17108, 1998.
14. Grassilli, E., M. A. Desiderio., E. Bellesia., P. Salomoni., F. Benatti, and C. Franceschi. Is polyamine decrease a common feature of apoptosis? Evidence from gamma rays- and heat-induced cell death. Biochem. Biophys. Res. Commun. 126, 708–714, 1995.
15. Grossmann, J., S. Mohr, E. G. Lapetina, C. Fiocchi, and A. D. Levin. Sequential and rapid activation of select caspases during apoptosis of normal intestinal epithelial cells. Am. J. Physiol. 274 (Gastrointest. Liver Physiol.37): G1117–G1124, 1998.
16. Halem, A., S. Takehiko, I. Kozieradzki, and J. M. Penninger. The cyclin-dependent kinase cdk2 regulates thymocyte apoptosis. J. Exp. Med., 189: 957–967, 1999.
17. Heby, O., and L. Presson. Molecular genetics of polyamine synthesis in eukaryotic cells. Trends Biochem. Sci. 15, 153–158, 1990.
18. Hermiston, M. L., and J. I. Gordon. In vivo analysis of cadherin function in the mouse intestinal epithelium: essential roles in adhesion, maintenance of differentiation, and regulation of programmed cell death. J. Cell Biol. 129: 489–506, 1995.
19. Hueber, A., P. Esser, K. Heimann, N. Kociok, S. Winter, and M. Weller. The topoisomerase I inhibitors, camptothecin and beta-lapachone, induce apoptosis of human retinal pigment epithelial cells. Exp Eye Res. 67: 525–530, 1998.
20. Kauffmann-Zeh, A., P. Rodriguez-Viciana, E. Ulrich, C. Gilbert. P. Coffer, J. Downward, and G. Evan. Suppression of c-Myc-induced apoptosis by Ras signalling through PI(3)K and PKB. Nature 385: 544–548, 1997.
21. Kinoshita, T., T. Yokota, K. Arai, and A. Miyajima. Regulation of Bcl-2 expression by oncogenic Ras protein in hematopoietic cells. Oncogene 10: 2207–2210, 1995.
22. Kothakota S., T. Azuma, C. Reinhard, A. Klippel, J. Tang, K. Chu, T. J. McGarry, M. W. Kirschner, K. Koths, D. J. Kwiatkowski, and L. T. Williams. Caspase-3 generated fragment of gelsolin: effect of morphological change in apoptosis. Science 278: 294-298, 1997.

23. Krasnow, M. A., and Cozzarelli, N. R. Catenation of DNA rings by topoisomerases. Mechanism of control by spermine. J. Biol. Chem. 257, 2687–2693, 1982.
24. Kuida, K., J. A. Lippke, G. Ku, M. W. Harding, D. J. Livingston, M. S.-S. Su, and R. A. Flavell. Altered cytokine export and apoptosis in mice deficient in interleukin-1β converting enzyme. Science 267: 2000–2003, 1995.
25. Lahti, J. M., J. Xiang, L. S. Heath, D. Campana, and V. J. Kidd. PITSLRE protein kinase activity is associated with apoptosis. Mol. Cell. Biol. 15: 1–11, 1995.
26. Lin X. R., D. I. Wilkinson, and E. M. Farber. Camptothecin induces differentiation, tissue transglutaminase and apoptosis in cultured keratinocytes. Exp Dermatol. 7: 179–183, 1998.
27. Marton, L. J., and A. E. Pegg. Polyamines as targets for therapeutic intervention. Annu. Rev. Pharmacol. Toxicol. 35, 55–91, 1995.
28. Mashima, T., M. Naito, K. Noguchi, D. K. Miller, D. W. Nicholson, and T. Tsuruo. Actin cleavage by cpp-32/apopain during the development of apoptosis. Oncogene, 14: 1007–1012, 1997.
29. McCormack, S. A., M. J. Viar, and L. R. Johnson. Migration of EEC-6 cells: a model for mucosal healing. Am.J. Physiol.263(Gastrointest. liver physiol.26) G426–G435, 1992.
30. McCormack, S. A., M. J. Viar, and L. R. Johnson. Polyamines are necessary for cell migration by a small intestinal crypt cell line. Am.J. Physiol. 274 (Gastrointest. liver physiol.27): G367–G374, 1993.
31. Meredith, J. E., Jr., B. Fazeli, and M. A. Schwartz. The extracellular matrix as a cell survival factor. Mol. Biol. Cell 4: 953–961, 1993.
32. Mitchell, J. L., R. R. Diveley Jr., A. Bareyal-Leyser, and J. L. Mitchell. Abnormal accumulation and toxicity of polyamines in a difluromethylornithine-resistant HTC cell variant. Biochim. Biophys. Acta, 1136:136–142, 1992.
33. Miura, M., H. Zhu, R. Rotello, E. A. Hartwieg, and J. Yuan. Induction of apoptosis in fibroblasts by IL-1β-converting enzyme, a mammalian homolog of the *C. elegans* cell death gene ced-3. Cell 75: 653–660, 1993.
34. Moss, S. F., B. Agrawal, N. Arber, R. J. Guan, M. Krajewska, S. Krajewski, J. C. Reed, P. R. Holt. Increased intestinal Bak expression results in apoptosis. Biochem. Biophys. Res. Commun. 223: 199–203, 1996.
35. Nicholson, D. W., and N. A. Thornberry. Caspases: killer proteases. Trends Biochem. Sci. 22: 299–306, 1997.
36. Packham, G., and J. L. Cleveland. Ornithine decarboxylase is a mediator of c-Myc induced apoptosis. Mol. Cell Biol. 14, 5741–5747, 1994.
37. Pegg, A. E. Polyamine metabolism and its importance in neoplastic growth and as a target for chemotherapy. Cancer Res. 48: 759–774, 1988.
38. Pegg, A. E; and Williams-Ashmann, H. G. Polyamines in Biology and Medicine (Morris, D. R; and Morton, L. J, eds.), New York: Marcel Dekker, 1981, p. 3–42.
39. Pelta J., F. Livolant, and J. Sikorav. DNA aggregation induced by polyamines and cobalthexamine. J. Biol. Chem. 271:5656–5662, 1996.
40. Penning, L. C., R. G. Schipper, D. Vercammen, A. J., Verhofstad, T. Denecker, R. Beyaer, and P. Vandenabeele. Sensitization of TNF-induced apoptosis with polyamine synthesis inhibitor in different human and murine tumor cell lines. Cytokines: 10:423431, 1998.
41. Pouline, R., J. K. Coward, J. R. Lakanen, and A. E. Pegg. Enhancement of the spermidine uptake system and lethal effects of spermidine overaccumulation in ornithine decarboxylase-overproducing L1210 cells under hypoosmotic stress. J. Biol. Chem. 268: 4690–4698, 1993.
42. Pouline, R., G. Pelletier, and A. E. Pegg. Induction of apoptosis by excessive polyamine accumulation in ornithine decarboxylase-overproducing L1210 cells. Biochem. J. 311: 723–727, 1995.
43. Quaroni, A; J. Wands; R. L. Trelstad; and K. J. Isselbacher. Epithelial cell culture from rat small intestine. J. Cell. Biol. 80: 248–265, 1988.
44. Rak, J., Y. Mitsuhashi, V. Erdos, S.-N. Huang, J. Filmus, and R. S. Kerbel. Massive programmed cell death in intestinal epithelial cells induced by three-dimensional growth conditions: suppression by mutant c-H-ras oncogene expression. J. Cell Biol. 131: 1587–1598, 1995.
45. Ray, R. M., B. J. Zimmerman, S. M. McCormack, T. B. Patel, and L. R. Johnson. Polyamine depletion arrests cell cycle and induces inhibitors p21 waf1/cip1, p27kip1, and p53 in IEC-6 cells. Am. J. Physiol 276 (Cell Physiol 45): C684–C691, 1999.
46. Re, F., A. Zanetti, M. Sironi, N. Polentarutti, L. Lanfrancone, E. Dejana, and F. Colotta. Inhibition of anchorage-dependent cell spreading triggers apoptosis in cultured human endothelial cells. J.Cell Biol. 127: 537–546, 1994.
47. Sane A. T., and R. Bertrand. Distinct steps in DNA fragmentation pathway during camptothecin-induced apoptosis involved caspase-, benzyloxycarbonyl- and N-tosyl-L-phenylalanylchloromethyl ketone-sensitive activities. Cancer Res. 58: 3066–3072, 1998.
48. Sarin, A., D. H. Adams, and P. A. Henkart. Protease inhibitors selectively block T cell receptor-triggered programmed cell death in a murine T cell hybridoma and activated peripheral T cells. J. Exp. Med. 278: 1693–1700, 1993.
49. Scheving, Lawrence A., Wen-Hui Jin, Kang-Mei Chong, Wendi Gardner, and Frederick O. Cope. Dying enterocytes downregulate signaling pathways converging on Ras: rescue by protease inhibition. Am. J. Physiol. 274 (Cell Physiol. 43): C1363–C1372, 1998.
50. Sinicrope, F. A., S. B. Ruan, K. R. Cleary, L. C. Stephens, J. J. Lee, and B. Levin. bcl-2 and p53 oncoprotein expression during colorectal tumorigenesis. Cancer Res. 55: 237–2411 1995.
51. Strater, J., K. Koretz, A. R. Gunthert, and P. Moller. In situ detection of enterocytic apoptosis in normal colonic mucosa and in familial adenomatous polyposis. Gut 37: 819–825, 1995.
52. Strater, J., U. Wedding, T. F. E. Barth, K. Koretz, C. Elsing, and P. Moller. Rapid onset of apoptosis in vitro follows disruption of β1-integrin/matrix interactions in human colonic crypt cells. Gastroenterology 110: 1776–1784, 1996.
53. Tabor, C. W., and Tabor, H. Polyamines. Annu. Rev. Biochem. 53: 749–790, 1984.
54. Thornberry, N. A., H. G. Bull, J. R. Calaycay, K. T. Chapman, A. D. Howard, M. J. Kostuva, D. K. Miller, S. M. Molineaut, J. R. Weidner, S. Aunins. A novel heterodimeric cysteine protease is required for interleukin-1 beta processing in monocytes. Nature. 356, 768–774, 1992.
55. Tobias, K. E., and C. Kahana. Exposure to ornithine results in excessive accumulation of putrescine and apoptotic cell death in ornithine decarboxylase overproducing mouse myeloma cells. Cell Growth Differ. 10: 1279–1285, 1995.
56. Tomei, L. D., J. P. Shapiro, and F. O. Cope. Apoptosis in C3H/10T1/2 mouse embryonic cells: evidence for internucleosomal DNA modification in the absence of double stranded cleavage. Proc. Natl. Acad. Sci. USA 90: 853-857, 1993.

57. Wang, J. Y; and L. R. Johnson. Role of ornithine decarboxylase in the repair process of gastric mucosal stress ulcers. Am. J. Physiol. 258: G78–G85, 1990.
58. Wang, J. Y., and L. R. Johnson. Luminal polyamines stimulate repair of gastric mucosal stress ulcers. Am. J. Physiol. 259 (Gastrointest. Liver Physiol. 22) G584–G592, 1990.
59. Wang, J. Y., and L. R. Johnson. Role of transglutaminase and protein cross linking in the repair of mucosal stress erosions. Am. J. Physiol. 262 (Gastrointest. Liver Physiol. 25): G818–G825, 1992.
60. Wang, J. Y; M. Viar; P. Blanner; and L. R. Johnson. Expression of the ornithine decarboxylase gene in response to asparagine in intestinal epithelial cells. Am. J. Physiol. 271: G164–G171, 1996.
61. Wang, J., and K. Walsh. Resistance to apoptosis conferred by cdk inhibitors during myocyte apoptosis. Science, 273: 359–361, 1996.
62. White, E. Life, death and the pursuit of apoptosis. Genes Dev. 10: 1–15, 1995.
63. Xie, X., M. E Tome, and E. W. Gerner. Loss of intracellular putrescine pool-size regulation induces apoptosis. Exp. Cell Res, 230: 386–392, 1997.
64. Yuan, J., S. Shaham, S. Ledoux, H. M. Ellis, H. R. Horvitz. The *C. elegans* cell death gene ced-3 encodes a protein similar to mammalian interleukin 1 beta-converting enzyme. Cell, 75: 641–652, 1993.

What is claimed is:

1. A method for reducing the death rate of non-cancerous intestinal cells in a patient that is to be treated by radiation therapy for a neoplastic condition, comprising administering to the patient an effective amount of an agent that results in the depletion of polyamines within the non-cancerous intestinal cells, and depleting the polyamines in the non-cancerous intestinal cells of the patient.

2. The method of claim 1 wherein the patient is a human patient.

3. The method of claim 1 wherein the patient is a non-human animal.

4. The method of claim 1 wherein the polyamine-depleting agent inhibits the action of ornithine decarboxylase.

5. The method of claim 4 wherein the agent is DL-œ-difluoromethylornithine.

6. The method of claim 1 wherein the radiation therapy is by x-ray or gamma irradiation.

* * * * *